United States Patent [19]
Lutz et al.

[11] Patent Number: 6,114,366
[45] Date of Patent: Sep. 5, 2000

[54] BROAD SPECTRUM PRESERVATIVE

[75] Inventors: Patrick J. Lutz, Easton; John Gerald Maroski, Bethlehem, both of Pa.

[73] Assignee: Lonza Inc., Fair Lawn, N.J.

[21] Appl. No.: 09/347,254

[22] Filed: Jul. 2, 1999

Related U.S. Application Data

[63] Continuation of application No. 08/807,763, Feb. 27, 1997, abandoned.

[51] Int. Cl.$^7$ .............................. A01N 43/50; A01N 43/80

[52] U.S. Cl. ........................... 514/372; 514/389; 514/391

[58] Field of Search ..................................... 514/372, 389, 514/391

[56] References Cited

U.S. PATENT DOCUMENTS 5,464,850  11/1995  Voo et al. ................................ 514/372
5,631,273  5/1997  Merianos ................................ 514/389

FOREIGN PATENT DOCUMENTS 9317558  9/1993  WIPO .

*Primary Examiner*—Allen J. Robinson
*Attorney, Agent, or Firm*—Darby & Darby

[57] ABSTRACT

The present invention relates to compositions containing a preservative system containing a two biocidal components, a first component comprising a formaldehyde donor compound, and the second component comprising one or more isothiazolone compounds, where the weight ratio of the first component to the second component ranges from about 1:1 to about 10,000:1.

20 Claims, No Drawings

BROAD SPECTRUM PRESERVATIVE

This is a continuation of application Ser. No. 08/807,763, filed Feb. 27, 1997, now abandoned.

BACKGROUND OF THE INVENTION

The need for effective and economical preservative compositions is well known. There are a wide variety of applications where inhibiting the growth of microorganisms is necessary, as for example personal care products such as shampoos, creams, lotions, cosmetics, and soaps and household products such as laundry detergents, hard surface cleaners, fabric softeners, and the like. The shelf life of these compositions depends on their resistance to microbial spoilage.

In addition, in many industrial compositions, antimicrobial agents are useful in paint, wood, textiles, adhesives, sealants, leather, rope, paper pulp, plastics, fuel, oil, and rubber and metal working fluids. The control of slime-producing bacteria and fungi in pulp and paper mills and in cooling towers is also a matter of substantial commercial importance.

Certain compounds have long been known to be useful as preservatives. Compounds such as the halopropynyl carbamates are known for their fungicidal activity; however, they are costly and, as a result, have only found applications in specialty areas where the high costs can be justified.

Other commercially known preservatives include Quaternium-15 (Dowicil 200, a trademark of Dow Chemical Company). It has the disadvantage of being a solid product which must be solubilized in water before it can be used in the end product. In aqueous solution it exhibits pH drift and causes formulation problems, particularly with regard to viscosity and color.

Formaldehyde in the free state, as in formalin, is effective only for short periods of time. In addition, it is inactivated by protein.

Alkyl parabens (e.g., methyl, ethyl, and propyl), which are useful as fungicides, have limited bactericidal action. They are generally solubilized in oil since they are poorly soluble in water, leading to formulation difficulties for personal care and household products. They are often inactivated by commonly used materials such as gelatin, methyl cellulose, and polyethylene glycol.

These preservatives have also included formaldehyde and isothiazolinone derivatives. U.S. Pat. No. 3,987,184 shows the use of 1,3-dimethylol-5,5-dimethylhydantoin (DMDMH) as a useful formaldehyde donor compound for the preservation of personal care products, cosmetics, and household and industrial products. Mixtures of 5-chloro-2-methyl-3-isothiazolin-4-one (CMI) and 2-methyl-3-isothiazolin-4-one (MI) have also been used to preserve personal care, household, and industrial products. While useful for controlling bacteria, fungi and other contamination in the products, these substances may be irritating and difficult to handle in the manufacture of end-use products such as shampoos.

More recently, less toxic substances have been used as preservatives, including iodopropynyl butylcarbamate, polyaminopropyl biguanide, bis(3-aminopropyl) dodecylamine, benzethonium chloride, methyldibromo glutaronitrile, and ethylene-diaminetetraacetic acid. However, to obtain full microbiological control, a greater amount of these preservatives must be added to the product, thereby making it more difficult to formulate. Also, when large amounts of additive are used, the likelihood of a negative impact on that product, such as instability, odor and breakdown of product, is greater. Moreover, some of these compounds, such as iodopropynyl butylcarbamate, are costly, so the use of large amounts of these compounds is not economical.

In light of the foregoing, it is clearly desirable to formulate a preservative which completely controls microbiological and fungal contamination in personal care products such as shampoos, conditioners and moisturizers, in household products with potential for contact with human skin and clothing, and in industrial products. The preservative should be easy to formulate and should be able to be used at levels low enough so as not to negatively impact the product. Also the preservative must be nontoxic and non-irritating at the levels used if it is to be used in personal care products, such as cosmetics and shampoos.

SUMMARY OF THE INVENTION

It has now been surprisingly and unexpectedly discovered that a synergistic combination of a first component comprising a formaldehyde donor compound, preferably an alkanoldialkyl hydantoin, and a second component comprising one or more 3-isothiazolone compounds gives both broad spectrum bactericidal and fungicidal activity suitable for use in personal care, household, and industrial products. A particularly surprising aspect of the invention is that the 3-isothiazolone component can be present in the final composition (i.e., the product to be preserved) at a concentration below 1 part per million (ppm) and still provide outstanding bactericidal and fungicidal activity. This activity could in no way be predicted based on the known biocidal effects of the components individually.

More specifically, the present invention relates to a preservative system and compositions comprising the preservative system, where the system comprises two biocidal components, a first component comprising a formaldehyde donor compound, preferably an alkanoldialkyl hydantoin, and the second component comprising one or more 3-isothiazolone compounds, where the weight ratio of the first component to the second component ranges from about 1:1 to about 10,000:1. Preferably, the ratio of the first component to the second component is from about 300:1 to about 1000:1. Preferably, the concentration of the second component in the composition is between about 0.05 and about 0.9 parts per million. More preferably, the concentration of the second component is between about 0.05 and 0.5 parts per million.

By combining these two components in compositions which require protection against microbial attack, a preservative system which completely controls microbiological contamination is obtained. Furthermore, due to the synergistic effect of the components, much less active material of each component is required as opposed to when each component is used alone. Accordingly, the preservative system of the present invention is easier to use and is less likely to have any toxic or skin sensitizing effects on individuals exposed to the product. A further advantage of the preservative system of the present invention is that it is able to fully control a broader spectrum of bacteria and fungi than any of the individual components. Another advantage is that the preservative system is more economical because lesser amounts of more expensive components are necessary.

A preservative system for clinical chemistry reagents comprising DMDMH and CMI/MI is disclosed by Voo et al. in U.S. Pat. No. 5,464,850. Clinical chemistry reagents typically are much easier to preserve than the compositions of the present invention, in that clinical chemistry reagents typically have a low, well-defined solids content (usually less than two percent), while personal care, household, and industrial compositions usually have a fairly high surfactant solids content (typically greater than 20 percent, most frequently from 20 to 30 percent). Most surfactant solids are good nutrients for microorganisms. Thus, the ability of the present preservative system to be used with 3-isothiazolone concentrations of less than 1 ppm would not have been expected from the teachings of Voo et al., which require the use of greater than 1 ppm of the 3-isothiazolone component for the preservation of compositions with very low solids content.

The broader ranges of formaldehyde donor compound to 3-isothiazolone ratios of the present invention also provide unexpected advantages over Voo et al., particularly with regard to the applications in which the preservative system is useful. Personal care formulations and household and industrial products are frequently complex, two phase oil and water emulsions. Partition effects between phases require the flexibility to use broad ranges of preservative component ratios, beyond those taught by Voo et al. The wide range of pH that is present in different personal care and household and industrial products, as opposed to the fixed pH 7.3 of the clinical chemistry reagent of Voo et al., also requires the broader range of preservative system component ratios of the present invention. Thus, Voo et al. does not teach or suggest the utility of a preservative system comprising alkanoldialkyl hydantoin and 3-isothiazolone for compositions other than clinical chemistry reagents.

The compositions of the invention include shampoos which include the preservative system. The preservatives can be added to the shampoos already formulated or the two components can be added to the shampoo separately. A wide variety of shampoo formulations can benefit from the practice of the present invention.

A further embodiment of the present invention is a conditioner for hair which includes the preservative system. Again the preservatives in combination can be added to the hair conditioner formulation or the two components can be added separately. Conditioners of many formula compositions can be used.

Yet another embodiment of the present invention is a moisturizer for skin which includes the preservative system. The two preservatives can be added together to the formulation or separately. Moisturizers of many formula compositions can be used.

Other embodiments of the invention include household products such as detergents, hard surface cleaners, fabric softeners, and the like, which contain the two component preservative system, as well as industrial products which contain the synergistic preservative system. Methods for preserving personal care products, household products, and industrial products are also provided by the present invention.

DETAILED DESCRIPTION OF THE INVENTION

The first component of the synergistic preservative system of the invention comprises a formaldehyde donor compound such as a hydantoins, N,N"-methylene bis[N'-(hydroxymethyl)-2,5-dioxo-4-imidazolidinyl]urea,N'-(hydroxymethyl)-N-(1,3-dihydroxymethyl-2,5-dioxo-4-imidazolidinyl]-N'-(hydroxymethyl)urea, and Quaternium-15. Preferred are alkanoldialkyl hydantoins having the formula:

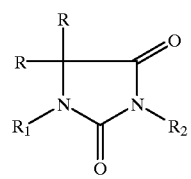

wherein each R is independently hydrogen, a methyl group, an ethyl group, a propyl group, or an aryl group, and $R_1$ and $R_2$ are each independently hydrogen or $(CH_2)OH$, with the proviso that both $R_1$ and $R_2$ cannot be hydrogen, and where the compound has chemical and physical characteristics compatible with use in personal care products. A preferred alkanoldialkyl hydantoin is 1,3-dimethylol-5,5-dimethylhydantoin (DMDMH).

The second component of the synergistic preservative system of the invention comprises one or more 3-isothiazolones having the formula:

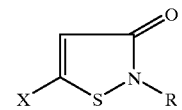

wherein X is hydrogen or halogen, preferably chlorine, and R is an alkyl chain of from 1 to 22 carbon atoms. The second component is typically obtained by diluting an aqueous stock solution that contains one or more 3-isothiazolones of the above formula, the stock solution generally being at a concentration of about 15 percent weight to volume, into the final formulated product in which the system acts as a preservative. A preferred second component is a mixture of 5-chloro-2-methyl-4-isothiazolin-3-one and 2-methyl-4-isothiazolin-3-one (CMI/MI).

The composition of a typical personal care formulation which can be effectively preserved by the synergistic system of the present invention, a protein shampoo, is detailed below in Table 1.

TABLE 1

Formulation of Protein Shampoo

| Component | Percent |
| --- | --- |
| Sodium lauryl ether (2) sulfate | 35 |
| TEA lauryl sulfate | 25 |
| Cocodiethanolamide | 3 |
| Hydrolyzed animal protein | 1 |
| Preservative | q.s. |
| Water, deionized | 36 |

To formulate this shampoo, all of the ingredients except the preservative are added to water and heated to 65° C. The preservative is added to achieve a clear solution while cooling to room temperature with stirring. If needed, the pH of the shampoo is adjusted to pH 7.0 with a solution of 50% citric acid.

Preferably, the components of the synergistic preservative system of the invention are added to the personal care formulation in amounts such that the final concentration of the second component (3-isothiazolone) is less than 1 part per million, and the ratio of the first component to the second component ranges between about 1:1 and about 10,000:1. More preferably, the ratio of the first component to the second component is between about 300:1 and about 1000:1. A more preferred range for the concentration of the second component of the system in the compositions to be preserved is between about 0.05 ppm and about 0.9 ppm. A preferred range for the concentration of the first component of the system is between about 200 ppm and about 500 ppm.

The following example is illustrative of the present invention, however, it will be understood that the invention is not limited to the specific details set forth in the example.

COMPARATIVE EXAMPLE

Evaluation of DMDMH and CMI/MI Alone Against Bacteria and Fungi

Mixed bacteria challenge tests were performed by adding approximately $1–5 \times 10^6$ organisms per gram of formulation, the organisms comprising an equally divided mixture of *Staphylococcus aureus* (ATCC No. 6538), *Pseudomonas aeruginosa* (ATCC No. 9027), and *Escherichia coli* (ATCC No. 8739) incubated at ~36° C. on nutrient agar slants 24 hours prior to testing. The test samples were incubated at ~23° C. (room temperature) for the number of days indicated, after which an aliquot of the sample was taken and diluted stepwise to a $10^6$ fold reduction in concentration. The diluted samples were plated out on tryptic soy agar and incubated for 48 hours at ~36° C. After incubation, readings of the total number of colonies per gram (cfu/g) were made on the samples. Table 2 illustrates the levels at which the individual components DMDMH and CMI/MI are effective and ineffective against bacteria.

Mixed fungal challenge tests were performed as follows. Forty grams of the formulation containing various concentrations of preservatives was inoculated with *Candida albicans* (ATCC No. 10231) and *Aspergillus niger* (ATCC No. 16404) in the case of the mixed fungi test, at a cell count of approximately $1–5 \times 10^5$ organisms per gram of formulation. Test samples were incubated at ~23° C. (room temp.) for a total of 28 days. A one gram aliquot was taken from each sample on the days indicated in the tables below, and diluted stepwise to a $10^6$ fold reduction in concentration. Each diluted sample was plated out in sabouraud dextrose agar and incubated for three to seven days at ~26° C. After incubation, readings of the number of colonies per gram (cfu/g) were made from the samples.

Table 3 illustrates the effects of CMI-MI and DMDMH individually against fungi, for comparative purposes.

TABLE 2

COMPARATIVE PRESERVATIVE CHALLENGE RESULTS FOR DMDMH OR CMI/MI IN PROTEIN SHAMPOO AGAINST MIXED BACTERIA[1]

| SAMPLE REFERENCE LONZA | PRESERVATIVE COMPONENT | TARGET ppm | COLONY COUNTS (CFU/ML) AT DAY INDICATED | | | | |
|---|---|---|---|---|---|---|---|
| | | | DAY 0 | DAY 7 | DAY 14 | DAY 21 | DAY 28 |
| 5309:188-2 | CMI-MI | 3.30 | $4.9 \times 10^6$ | <10 | <10 | <10 | <10 |
| 5309:188-1 | CMI-MI | 1.65 | $3.9 \times 10^6$ | <10 | <10 | <10 | <10 |
| 5309:188-6 | DMDMH | 720 | $3.5 \times 10^6$ | <10 | <10 | <10 | <10 |
| 5309:188-5 | DMDMH | 420 | $3.3 \times 10^6$ | <10 | <10 | <10 | <10 |
| 5309:188-4 | DMDMH | 120 | $4.2 \times 10^6$ | <10 | <10 | <10 | <10 |
| 5309:188-3 | DMDMH | 60 | $5.5 \times 10^6$ | $6.9 \times 10^4$ | <10 | <10 | <10 |
| 5309:188-8 | NONE | 0 | $5.1 \times 10^6$ | $1.9 \times 10^6$ | $3.7 \times 10^7$ | $9.1 \times 10^7$ | $2.8 \times 10^8$ |

[1] An equal mixture of *E. coli* 8739, *S. aureus* 6538 and *P. aeruginosa* 9027.

TABLE 3

COMPARATIVE PRESERVATIVE CHALLENGE RESULTS FOR DMDMH AND CMI/MI INDIVIDUALLY IN PROTEIN SHAMPOO AGAINST MIXED FUNGI[2]

| SAMPLE REFERENCE LONZA | PRESERVATIVE COMPONENT | TARGET ppm | COLONY COUNTS (CFU/ML) AT DAY INDICATED | | | | |
|---|---|---|---|---|---|---|---|
| | | | DAY 0 | DAY 7 | DAY 14 | DAY 21 | DAY 28 |
| 5309:188-2 | CMI-MI | 3.30 | $1.1 \times 10^5$ | <10 | <10 | <10 | <10 |
| 5309:188-1 | CMI-MI | 1.65 | $1.1 \times 10^5$ | <10 | <10 | <10 | <10 |
| 5309:188-6 | DMDMH | 720 | $1.2 \times 10^5$ | <10 | <10 | <10 | <10 |
| 5309:188-5 | DMDMH | 420 | $1.1 \times 10^5$ | $2.4 \times 10^3$ | $1.6 \times 10^3$ | $6.9 \times 10^2$ | $3.0 \times 10^2$ |
| 5309:188-4 | DMDMH | 120 | $1.4 \times 10^5$ | $5.1 \times 10^4$ | $1.8 \times 10^4$ | $4.6 \times 10^3$ | $2.0 \times 10^3$ |
| 5309:188-3 | DMDMH | 60 | $1.1 \times 10^5$ | $5.3 \times 10^4$ | $6.2 \times 10^4$ | $1.2 \times 10^4$ | $3.0 \times 10^4$ |
| 5309:188-8 | NONE | 0 | $1.1 \times 10^5$ | $7.2 \times 10^4$ | $4.2 \times 10^4$ | $3.0 \times 10^4$ | $1.9 \times 10^4$ |

[2] An equal mixture of *C. albicans* 10231 and *A. niger* 16404

Comparative challenge results reported in Table 2 (mixed bacteria) and Table 3 (mixed fungi) show that 3.30 ppm and 1.65 ppm CMI-MI will control both mixed bacteria and mixed fungi by Day 7. The results in Tables 2 and 3 also show that DMDMH alone is more effective at controlling mixed bacteria than mixed fungi; at levels down to 60 ppm, DMDMH will control mixed bacteria by Day 14, but will not control mixed fungi. DMDMH alone at 720 ppm will control mixed fungi by Day 7, but is incapable of doing so at 420 ppm; this level (420 ppm) provides a baseline for use in synergistic systems with CMI-MI.

As shown in Table 3, 1.65 ppm of CMI-MI will effectively control mixed fungi at Day 7. To determine a CMI-MI level that did not control fungi for use as a baseline for use in synergistic systems with DMDMH, challenge experiments were performed as described above; the results are shown in Table 4.

TABLE 4

COMPARATIVE PRESERVATIVE CHALLENGE RESULTS FOR CMI/MI IN PROTEIN SHAMPOO AGAINST MIXED FUNGI TO DETERMINE LEVELS THAT DO NOT INHIBIT MIXED FUNGI[2]

| SAMPLE REFERENCE LONZA | PRESERVATIVE COMPONENT | TARGET ppm | COLONY COUNTS (CFU/ML) AT DAY INDICATED | | | | |
|---|---|---|---|---|---|---|---|
| | | | DAY 0 | DAY 7 | DAY 14 | DAY 21 | DAY 28 |
| 5410:39-1 | CMI-MI | 1.65 | $5.8 \times 10^4$ | <10 | <10 | <10 | <10 |
| 5410:39-2 | CMI-MI | 1.02 | $8.6 \times 10^4$ | <10 | <10 | <10 | <10 |
| 5410:39-3 | CMI-MI | 0.80 | $8.5 \times 10^4$ | $2.0 \times 10^2$ | <10 | <10 | <10 |
| 5410:39-4 | CMI-MI | 0.44 | $8.0 \times 10^4$ | $3.0 \times 10^4$ | $1.7 \times 10^4$ | $6 \times 10^3$ | $4.2 \times 10^3$ |
| 5410:39-5 | CMI-MI | 0.22 | $9.4 \times 10^4$ | $5.3 \times 10^4$ | $5.2 \times 10^4$ | $3.1 \times 10^4$ | $7.1 \times 10^3$ |
| 5410:39-6 | NONE | 0 | $8.2 \times 10^4$ | $3.8 \times 10^4$ | $4.0 \times 10^4$ | $4.2 \times 10^4$ | $3.0 \times 10^4$ |

[2]An equal mixture of C. albicans 10231 and A. niger 16404

Challenge results shown in Table 4 indicate that at 0.80 ppm, CMI-MI will control mixed fungi by Day 14. However, CMI-MI at 0.44 ppm will not control mixed fungi at all. Thus, the 0.44 ppm level of CMI-MI was used as a starting point for determining synergies between DMDMH and CMI-MI.

EXAMPLE 1

Synergistic Effect of Combining DMDMH and CMI/MI in a Preservative System

The challenge results shown in Table 5 confirm that individually, neither DMDMH at 420 ppm nor CMI-MI at 0.44 ppm will control mixed fungi. However, a composition with 420 ppm of DMDMH and 0.44 ppm of CMI-MI in combination will control mixed fungi by Day 3, clearly demonstrating a synergistic effect. The results in Table 5 also demonstrate that levels as low as 204 ppm of DMDMH in combination with 0.22 ppm of CMI-MI controlled mixed fungi by Day 3.

TABLE 5

PRESERVATIVE CHALLENGE RESULTS FOR DMDMH AND CMI/MI IN PROTEIN SHAMPOO AGAINST MIXED FUNGI[2]

| SAMPLE REFERENCE LONZA | PRESERVATIVE COMPONENT | TARGET ppm | COLONY COUNTS (CFU/ML) AT DAY INDICATED | | | | |
|---|---|---|---|---|---|---|---|
| | | | DAY 0 | DAY 3 | DAY 7 | DAY 14 | DAY 21 | DAY 28 |
| 5410:59-1 | DMDMH | 420 | $1.3 \times 10^5$ | $2.1 \times 10^3$ | $3.3 \times 10^3$ | $1.1 \times 10^3$ | $3.0 \times 10^2$ | $2 \times 10^1$ |
| 5410:59-2 | CMI-MI | 0.44 | $1.3 \times 10^5$ | $3.1 \times 10^4$ | $1.3 \times 10^4$ | $1.8 \times 10^4$ | $1.7 \times 10^4$ | $1.3 \times 10^4$ |
| 5410:59-3 | DMDMH CMI-MI | 420 0.44 | $1.3 \times 10^5$ | <10 | <10 | <10 | <10 | <10 |
| 5410:594 | DMDMH CMI-MI | 303 0.30 | $1.2 \times 10^5$ | <10 | <10 | <10 | <10 | <10 |
| 5410:59-5 | DMDMH CMI-MI | 204 0.22 | $1.3 \times 10^5$ | <10 | <10 | <10 | <10 | <10 |
| 5410:59-6 | NONE | 0 | $1.2 \times 10^5$ | $11.1 \times 10^5$ | $1.1 \times 10^5$ | $1.0 \times 10^5$ | $1.0 \times 10^5$ | $3.4 \times 10^5$ |

[2]An equal mixture of C. albicans 10231 and A. niger 16404

The ability of levels of DMDMH and CMI-MI which could act synergistically to control mixed fungi were then assayed for the ability to control mixed bacteria. The results are shown in Table 6.

TABLE 6

PRESERVATIVE CHALLENGE RESULTS FOR DMDMH AND CMI/MI IN PROTEIN SHAMPOO AGAINST MIXED BACTERIA[1]

| SAMPLE REFERENCE LONZA | PRESERVATIVE COMPONENT | TARGET ppm | COLONY COUNTS (CFU/ML) AT DAY INDICATED | | | | | |
|---|---|---|---|---|---|---|---|---|
| | | | DAY 0 | DAY 3 | DAY 7 | DAY 14 | DAY 21 | DAY 28 |
| 5410:83-1 | DMDMH | 204 | $5.2 \times 10^6$ | <10 | <10 | <10 | <10 | <10 |
| | CMI-MI | 0.22 | | | | | | |
| 5410:53-2 | DMDMH | 105 | $5.6 \times 10^6$ | $7.3 \times 10^4$ | <10 | <10 | <10 | <10 |
| | CMI-MI | 0.11 | | | | | | |
| 5410:83-3 | DMDMH | 50 | $7.0 \times 10^6$ | $1.3 \times 10^5$ | $1.0 \times 10^2$ | <10 | <10 | <10 |
| | CMI-MI | 0.05 | | | | | | |
| 5410:83-4 | DMDMH | 25 | $6.6 \times 10^6$ | $5.4 \times 10^5$ | $2.2 \times 10^4$ | $7.1 \times 10^6$ | TNTC | TNTC |
| | CMI-MI | 0.025 | | | | | | |
| 5410:83-6 | NONE | 0 | $6.8 \times 10^6$ | $11.3 \times 10^6$ | $5.2 \times 10^6$ | $2.0 \times 10^7$ | TNTC | TNTC |

[1]An equal mixture of *E. coli* 8739, *S. aureus* 6538 and *P. aeruginosa* 9027.

Challenge results shown in Table 6 illustrate that DMDMH at 204 ppm in combination with CMI-MI at 0.22 ppm will control mixed bacteria as well as mixed fungi by Day 3. These levels are clearly significantly below the levels of the individual biocides which are effective for controlling fungi or bacteria, and so the present invention provides a preservative system that, when used in personal care formulations, will expose the user of the formulation to significantly less of either biocide than if the biocide were used as the sole preservative of the formulation.

Further experiments were performed to determine the lowest effective concentration limits for inhibiting fungal growth of the components of the synergistic preservative system of the invention. These results are shown in Table 7.

3-isothiazolone, greater levels of alkanoldialkyl hydantoin, which is still not effective alone to inhibit the growth of fungi, can be used. For example, preservative systems which comprise up to about 500 ppm of a alkanoldialkyl hydantoin and as low as 0.05 ppm of 3-isothiazolone are also within the scope of the invention, and are effective to inhibit the growth of both bacteria and fungi.

Thus, the preservative system described herein is unique in the art in that it provides a method for preserving a wide variety of compositions, i.e., personal care, household products, and industrial products, against bacterial and fungal contamination, while at the same time keeping the concentration of 3-isothiazolone extremely low, and in most cases below 1 part per million, 3-isothiazolones, and particularly CMI-MI, are powerful preservatives, but have the disadvantage of being skin sensitizers. Thus, preservative systems such as the present invention which require less 3-isothiazolone for their effectiveness are advantageous relative to those which require greater amounts. In addition,

TABLE 7

PRESERVATIVE CHALLENGE RESULTS FOR DMDMH AND CMI/MI IN PROTEIN SHAMPOO AGAINST MIXED FUNGI TO DETERMINE LEVELS OF COMBINED AGENTS THAT WILL NOT INHIBIT MIXED FUNGI[2]

| SAMPLE REFERENCE LONZA | PRESERVATIVE COMPONENT | TARGET ppm | COLONY COUNTS (CFU/ML) AT DAY INDICATED | | | | | |
|---|---|---|---|---|---|---|---|---|
| | | | DAY 0 | DAY 3 | DAY 7 | DAY 14 | DAY 21 | DAY 28 |
| 5410:83-1 | DMDMH | 204 | $1.5 \times 10^5$ | <10 | <10 | <10 | <10 | <10 |
| | CMI-MI | 0.22 | | | | | | |
| 5410:83-2 | DMDMH | 105 | $1.4 \times 10^5$ | $7.8 \times 10^4$ | $1.2 \times 10^5$ | $3.0 \times 10^4$ | $1.2 \times 10^4$ | $3.9 \times 10^3$ |
| | CMI-MI | 0.11 | | | | | | |
| 5410:83-3 | DMDMH | 50 | $1.3 \times 10^5$ | $1.2 \times 10^5$ | $1.0 \times 10^5$ | $7.7 \times 10^4$ | $3.6 \times 10^4$ | $3.1 \times 10^4$ |
| | CMI-MI | 0.05 | | | | | | |
| 5410:83-4 | DMDMH | 25 | $1.5 \times 10^5$ | $1.2 \times 10^5$ | $3.0 \times 10^5$ | $5.8 \times 10^4$ | $4.3 \times 10^4$ | $3.9 \times 10^4$ |
| | CMI-MI | 0.025 | | | | | | |
| 5410:83-6 | NONE | 0 | $1.3 \times 10^5$ | $1.4 \times 10^5$ | $1.0 \times 10^5$ | $8.6 \times 10^4$ | $5.7 \times 10^4$ | $3.7 \times 10^4$ |

[2]An equal mixture of *C. albicans* 10231 and *A. niger* 16404

Tables 6 and 7 also show that DMDMH at 105 ppm in combination with CMI-MI at 0.11 ppm will not control mixed fungi. However, 50 ppm DMDMH in combination with 0.05 ppm CMI-MI is effective in controlling mixed bacteria. When it is desirable to use extremely low levels of the ability of the present preservative system to preserve compositions with a high solids content, e.g., personal care products such as shampoos and household products that contain large amounts of detergents, is also an unexpected advantage of the present invention.

What is claimed is:

1. A personal care, household, or industrial product which comprises at least 20 percent solids and an antimicrobially synergistic mixture of a first component comprising a formaldehyde donor compound and a second component comprising one or more isothiazolone having the formula:

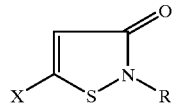

wherein X is hydrogen or halogen and R is an alkyl chain of from 1 to 22 carbon atoms and wherein the second compound is present in an amount of less than 1 ppm and the weight ratio of the first component to the second component ranges from about 1:1 to about 10,000:1.

2. The product of claim 1 wherein said first component comprises an alkanol-5,5-dialkylhydantoin having the formula:

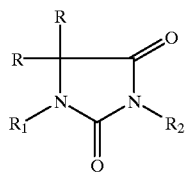

wherein each R is independently selected from the group consisting of hydrogen, methyl, ethyl, propyl, and aryl, and $R_1$ and $R_2$ are each independently hydrogen or $CH_2OH$, with the proviso that both $R_1$ and $R_2$ cannot be hydrogen.

3. The product of claim 2 wherein said weight ratio of said first component to said second component is from about 300:1 to about 1000:1.

4. The product of claim 2 wherein said product is a personal care product selected from the group consisting of shampoos, conditioners, creams, lotions, cosmetics, and soft soaps.

5. The product of claim 2 wherein said product is a household or industrial product selected from the group consisting of fabric softeners, laundry detergents, hard surface cleaners, air fresheners, polymer emulsions, water-based gels, natural latex, surfactant solutions, water-based paints, protective coatings, water-based adhesives, sealants and caulks, latex for paper coating, water-based inks, metal-working fluids, emulsion-based metal cleaning fluids used in electroplating, phosphatizing, galvanizing and general metal cleaning operations, hydraulic fluids, and aqueous mineral slurries.

6. A personal care, household, or industrial product which comprises a detergent and an antimicrobially synergistic mixture of a first component comprising a formaldehyde donor compound and a second component comprising one or more isothiazolones having the formula:

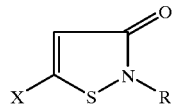

wherein X is hydrogen or halogen and R is an alkyl chain of from 1 to 22 carbon atoms and wherein the second component is present in an amount of less than 1 ppm and the weight ratio of the first component to the second component ranges from about 1:1 to about 10,000:1.

7. A personal care, household, or industrial product which comprises at least 20 percent solids and an antimicrobially synergistic mixture of a first component comprising 1,3-dimethylol-5,5-dimethylhydantoin and a second component comprising a mixture of 5-chloro-2-methyl-4-isothiazolin-3-one and 2-methyl-4-isothiazolin-3-one and wherein the second component is present in an amount less than 1 ppm and the weight ratio of the first component to the second component ranges from about 1:1 to about 10,000:1.

8. The product of claim 7 wherein said weight ratio of said first component to said second component is from about 300:1 to about 1000:1.

9. The product of claim 7 wherein said product is a personal care product selected from the group consisting of shampoos, conditioners, creams, lotions, cosmetics, and soft soaps.

10. The product of claim 7 wherein said product is a household or industrial product selected from the group consisting of fabric softeners, laundry detergents, hard surface cleaners, air fresheners, polymer emulsions, water-based gels, natural latex, surfactant solutions, water-based paints, protective coatings, water-based adhesives, sealants and caulks, latex for paper coating, water-based inks, metal-working fluids, emulsion-based metal cleaning fluids used in electroplating, phosphatizing, galvanizing and general metal cleaning operations, hydraulic fluids, and aqueous mineral slurries.

11. A personal care, household, or industrial product which comprises a detergent and an antimicrobially synergistic mixture of a first component comprising 1,3-dimethylol-5,5-dimethylhydantoin and a second component comprising a mixture of 5-chloro-2-methyl-4-isothiazolin-3-one and 2-methyl-4-isothiazolin-3-one and wherein the second component is present in an amount of less than 1 ppm and the weight ratio of the first component to the second component ranges from about 1:1 to about 10,000:1.

12. The product of claim 11 wherein said second component is present in said composition at a concentration of between about 0.05 and 0.9 ppm.

13. The product of claim 11 wherein said first component is present in said composition at a concentration of between about 200 and about 500 ppm.

14. The product of claim 11 wherein said second component is present in said composition at a concentration of between about 0.05 and 0.5 ppm.

15. A method for controlling the growth of microorganisms in a medium which comprises at least 20 percent solids which will support growth of microorganisms which comprises contacting said medium with a composition which comprises an antimicrobially synergistic mixture of a first component comprising a formaldehyde donor compound, and a second component comprising one or more isothiazolone having the formula:

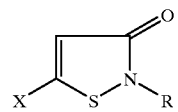

wherein X is hydrogen or halogen and R is an alkyl chain of from 1 to 22 carbon atoms and wherein the second component is present in an amount of less than 1 ppm and the weight ratio of the first component to the second component ranges from about 1:1 to about 10,000:1.

16. The method of claim 15 wherein said second component is present in said composition at a concentration of between about 0.05 and about 0.9 ppm.

17. The method of claim 15 wherein said first component is present in said composition at a concentration of between about 200 ppm and about 500 ppm.

18. A method for controlling the growth of microorganisms in a medium which comprises at least 20 percent solids which will support growth of microorganisms which comprises contacting said medium with a composition which comprises an antimicrobially synergistic mixture of a first component comprising 1,3-dimethylol-5,5-dimethylhydantoin and a second component comprising a mixture of 5-chloro-2-methyl-4-isothiazolin-3-one and 2-methyl-4-isothiazolin-3-one and wherein the second component is present in an amount of less than 1 ppm and the weight ratio of the first component to the second component ranges from about 1:1 to about 10,000:1.

19. The method of claim 18 wherein said second component is present in said composition at a concentration of between about 0.05 and about 0.9 ppm.

20. The method of claim 18 wherein said first component is present in said composition at a concentration of between about 200 ppm and about 500 ppm.

* * * * *